US007071166B2

(12) United States Patent
Nishida et al.

(10) Patent No.: US 7,071,166 B2
(45) Date of Patent: Jul. 4, 2006

(54) SKIN WOUND HEALING PROMOTERS

(75) Inventors: Teruo Nishida, 8-4, Asutopia 6-chome, Ube-shi, Yamaguchi 755-0152 (JP); Katsuhiko Nakata, Ikoma (JP); Masatsugu Nakamura, Ikoma (JP)

(73) Assignees: Santen Pharmacetical Co., Ltd., Osaka (JP); Teruo Nishida, Ube (JP)

( * ) Notice: Subject to any disclaimer, the term of this patent is extended or adjusted under 35 U.S.C. 154(b) by 0 days.

(21) Appl. No.: 10/344,199

(22) PCT Filed: Aug. 10, 2001

(86) PCT No.: PCT/JP01/06933

§ 371 (c)(1),
(2), (4) Date: Feb. 7, 2003

(87) PCT Pub. No.: WO02/13853

PCT Pub. Date: Feb. 21, 2002

(65) Prior Publication Data

US 2003/0181386 A1 Sep. 25, 2003

(30) Foreign Application Priority Data

Aug. 10, 2000 (JP) .............................. 2000-24289
Nov. 28, 2000 (JP) ............................ 2000-361388

(51) Int. Cl.
*A61K 38/00* (2006.01)
(52) U.S. Cl. ..................................................... 514/15
(58) Field of Classification Search ................... 514/15
See application file for complete search history.

(56) References Cited

U.S. PATENT DOCUMENTS

| 3,862,114 | A |   | 1/1975 | Scandrett |         |
|-----------|---|---|--------|-----------|---------|
| 5,616,562 | A | * | 4/1997 | Murphy et al. | 514/15 |
| 6,221,846 | B1| * | 4/2001 | Nishida et al. | 514/5 |

FOREIGN PATENT DOCUMENTS

| EP | 0 280 460 A | 8/1988 |
| EP | 280460 A | 8/1988 |
| EP | 493985 A | 7/1992 |
| EP | 0493985 A | 7/1992 |
| EP | 0558751 A | 9/1993 |
| EP | 558751 A | 9/1993 |
| EP | 0 914 827 A | 5/1999 |
| EP | 914827 A | 5/1999 |
| JP | 10-17489 A | 1/1998 |
| WO | WO 95/13087 A | 5/1995 |
| WO | 49419 | * 12/1997 |
| WO | WO 97/49419 | * 12/1997 |

OTHER PUBLICATIONS

Nakamura et al. Synergistic effect with Phe-Gly-Leu-Met-NH2 of the C-terminal of substance P and insulin-like growth factor-1 on epithelial wound healing of rabbit cornea. Br J Pharmacol. May 1999;127(2):489-97.*

Bhora et al. Effect of growth factors on cell proliferation and epithelialization in human skin. J Surg Res. Aug. 1995;59(2):236-44.*

McGovern et al. Intracellular calcium as a second messenger following growth stimulation of human keratinocytes. Br J Dermatol. Jun. 1995;132(6):892-6.*

Database MEDLINE on STN, U.S. national Library of Medicine, DN: 97243905 (Abstract), M. Nakamura et al, "Combined Effects of Substance P and Insulin-Like Growth Factor-1, on Corneal Epithelial Wound Closure of Rabbit in Vivo", *Current Eye Research*, vol. 16, No. 7, pp. 275-278 (1997).

F.Y. Bhora et al, "Effect of Growth Factors on Cell Proliferation and Epithelialization in Human Skin", *Journal of Surgical Research*, vol. 59, No. 2, pp. 236-244 (1995).

U.B. McGovern et al, "Intracellular Calcium as a Second Messenger Following Growth Stimulation of Human Keratinocytes", *British Journal of Dermatology*, vol. 132, No. 6, pp. 892-896 (1995).

M. Nakamura et al, "Combined effects of substance P and insulin-like growth factor-1 on corneal epithelial wound closure of rabbit in vivo", *Current Eye Research*, vol. 16, No. 7, pp. 275-278 (1997).

F. Y. Bhora et al, "Effect of Growth Factors on Cell Proliferation and Epithelialization in Human Skin", *Journal of Surgical Research*, vol. 59, No. 2, pp. 236-244 (1995).

U. B. McGovern et al, "Intracellular calcium as a second messenger following growth stimulation of human keratinocytes", *British Journal of Dermatology*, vol. 132, No. 6, pp. 892-896 (1995).

Y. Inoue et al, "The Sequential Changes of Substance P During Acute Herpetic Keratitis in Mice", *J. Jpn. Apthalmol. Soc.*; vol. 91, pp. 982-987 (1987).

t. Katayama, "Ocular Inflammation and Neuropeptides in Rabbit Ocular Tissue", *J. Jpn. Opthalmol. Soc.*, vol. 92, pp. 448-452 (1988).

NO. Takasu et al, "Insulin-like Growth Factor I Stimulates Inositol Phosphate Accumulation, a Rise in Cytoplasmic Free Clacium, and Proliferation in Cultures Porcine Thyroid Cells", *J. Biol. Chem.*, vol. 264, No. 31, pp. 18485-18488 (1989).

P. V. Pedone et al, "Mono- and bi-allelic expression of insulin-like growth factor II gene in human muscle tumors", *Hum. Mol. Genet.*, vol. 3, No. 7, pp. 1117-1121 (1994).

* cited by examiner

Primary Examiner—Christopher R. Tate
Assistant Examiner—Maury Audet
(74) *Attorney, Agent, or Firm*—Frishauf, Holtz, Goodman & Chick, P.C.

(57) ABSTRACT

The present invention provides healing promoters for skin wounds such as rupture, abrasion, surgical incision, skin ulcer and burn. Coexistence of Arg-Pro-Lys-Pro-Gln-Gln-Phe-Phe-Gly-Leu-Met-$NH_2$ (SEQ ID NO: 1) or Phe-Gly-Leu-Met-$NH_2$ (SEQ ID NO: 2) with insulin-like growth factor-I exhibits a remarkable promotive action on healing the skin wounds. Accordingly, combined administration of at least one of the substance P analogs and pharmaceutically acceptable salts thereof with the insulin-like growth factor exhibits a promotive effect on epidermal extension and a promotive effect on healing the skin wounds.

12 Claims, No Drawings

```
                             SEQUENCE LISTING

<160> NUMBER OF SEQ ID NOS: 16

<210> SEQ ID NO 1
<211> LENGTH: 11
<212> TYPE: PRT
<213> ORGANISM: Human

<400> SEQUENCE: 1

Arg Pro Lys Pro Gln Gln Phe Phe Gly Leu Met
1               5                   10

<210> SEQ ID NO 2
<211> LENGTH: 4
<212> TYPE: PRT
<213> ORGANISM: Human

<400> SEQUENCE: 2

Phe Gly Leu Met
1

<210> SEQ ID NO 3
<211> LENGTH: 12
<212> TYPE: PRT
<213> ORGANISM: Human

<400> SEQUENCE: 3

Tyr Arg Pro Lys Pro Gln Gln Phe Phe Gly Leu Met
1               5                   10

<210> SEQ ID NO 4
<211> LENGTH: 11
<212> TYPE: PRT
<213> ORGANISM: Human

<400> SEQUENCE: 4

Arg Pro Lys Pro Gln Gln Phe Tyr Gly Leu Met
1               5                   10

<210> SEQ ID NO 5
<211> LENGTH: 9
<212> TYPE: PRT
<213> ORGANISM: Human

<400> SEQUENCE: 5

Tyr Pro Gln Gln Phe Phe Gly Gln Met
1               5

<210> SEQ ID NO 6
<211> LENGTH: 8
<212> TYPE: PRT
<213> ORGANISM: Human

<400> SEQUENCE: 6

Pro Gln Gln Phe Phe Gly Leu Met
1               5
```

-continued

```
<210> SEQ ID NO 7
<211> LENGTH: 8
<212> TYPE: PRT
<213> ORGANISM: Human

<400> SEQUENCE: 7

Pro Gln Gln Phe Tyr Gly Leu Met
1               5

<210> SEQ ID NO 8
<211> LENGTH: 7
<212> TYPE: PRT
<213> ORGANISM: Human

<400> SEQUENCE: 8

Gln Gln Phe Phe Gly Leu Met
1               5

<210> SEQ ID NO 9
<211> LENGTH: 7
<212> TYPE: PRT
<213> ORGANISM: Human

<400> SEQUENCE: 9

Asp Ala Phe Tyr Gly Leu Met
1               5

<210> SEQ ID NO 10
<211> LENGTH: 6
<212> TYPE: PRT
<213> ORGANISM: Human

<400> SEQUENCE: 10

Gln Phe Phe Gly Leu Met
1               5

<210> SEQ ID NO 11
<211> LENGTH: 6
<212> TYPE: PRT
<213> ORGANISM: Human

<400> SEQUENCE: 11

Ala Phe Tyr Gly Leu Met
1               5

<210> SEQ ID NO 12
<211> LENGTH: 5
<212> TYPE: PRT
<213> ORGANISM: Human

<400> SEQUENCE: 12

Phe Phe Gly Leu Met
1               5

<210> SEQ ID NO 13
<211> LENGTH: 5
<212> TYPE: PRT
<213> ORGANISM: Human

<400> SEQUENCE: 13

Tyr Phe Gly Leu Met
1               5
```

-continued

```
<210> SEQ ID NO 14
<211> LENGTH: 5
<212> TYPE: PRT
<213> ORGANISM: Human

<400> SEQUENCE: 14

Gly Phe Gly Leu Met
1               5

<210> SEQ ID NO 15
<211> LENGTH: 4
<212> TYPE: PRT
<213> ORGANISM: Human

<400> SEQUENCE: 15

Phe Gly Leu Met
1

<210> SEQ ID NO 16
<211> LENGTH: 4
<212> TYPE: PRT
<213> ORGANISM: Human

<400> SEQUENCE: 16

Tyr Gly Leu Met
1
```

SKIN WOUND HEALING PROMOTERS

This application is a U.S. National Phase Application under 35 U.S.C. 371 of International Application No. PCT/JP01/06933 (not published in English) filed Aug. 101 2001.

TECHNICAL FIELD

The present invention relates to skin wound healing promoters comprising at least one of substance P analogs and pharmaceutically acceptable salts thereof and an insulin-like growth factor as active ingredients.

BACKGROUND ART

Skin wounds are damage of surface tissues such as rupture, abrasion, surgical incision, skin ulcer or burn. General treatment of these skin wounds is to give first aid to wounded sites and then to wait spontaneous recovery due to restoration of a living body.

However, such spontaneous recovery requires a long period until restoration, and pains also continue. Accordingly, it is desirable to promote wound healing positively by administering therapeutic agents for wounds to the wounded sites.

Since new epithelial tissues and connective tissues are formed by migration and proliferation of cells in a healing process of wounds, drugs which promote or stimulate migration, differentiation and proliferation of cells participates in wound healing can be therapeutic agents for wounds. Lysozyme chloride, solcoseryl and the like are known as these therapeutic agents for wounds.

However, existing therapeutic agents for wounds entail the problems that the agents do not exhibit sufficient promotive actions on wound healing and cannot recover the wounds completely for a short period. These problems are considered to be due to small contribution of these agents to recoverage of epidermis, synthesis of collagen, improvement of peripheral circulation, granulation formation, angiogenesis or the like, which is an important factor in the healing process of wounds.

Substance P analogs are polypeptides consisting of three to twelve amino acids which are disclosed specifically in U.S. Pat. No. 3,862,114, and these polypeptides are known to have hypotensive actions. Substance P, which is one of the substance P analogs, is a polypeptide released and formed from a neural terminal, is a polypeptide consisting of eleven amino acids represented by the formula of Arg-Pro-Lys-Pro-Gln-Gln-Phe-Phe-Gly-Leu-Met-NH$_2$ (SEQ ID NO: 1) and is known to exhibit vasodilation, smooth muscle contraction, secretion promotion of salivary gland, a diuretic action and the like. In an ophthalmological field, there were reported an effect of substance P on improving abnormal secretion of conjunctival goblet cells in ophthalmic disorders (WO 95/13087), kinetics of substance P in inflammation such as keratitis (J. Jpn. Ophthalmol. Soc., 91, 982–987 (1987), J. Jpn. Ophthalmol. Soc., 92, 448–452 (1988)) and the like. Further, Japanese Laid-open Patent Publication No. 17489/1998 discloses that Phe-Gly-Leu-Met-NH$_2$ (SEQ ID NO: 2) (hereinafter referred to as "FGLM"), which is a tetrapeptide on a C-terminal side of substance P, has an effect as a therapeutic agent for corneal disorders.

On the other hand, an insulin-like growth factor is one of factors which adjust growth of normal human cells such as an epidermal growth factor, a fibroblast growth factor, a platelet-derived growth factor and a transforming growth factor and is classified into two groups, i.e., insulin-like growth factor-I (hereinafter referred to as "IGF-I") and insulin-like growth factor-II (hereinafter referred to as "IGF-II"). It was reported that IGF-I stimulates proliferation of thyroid cells (J. Biol. Chem., 264, 18485–18488 (1989)), IGF-II adjusts growth and differentiation of muscle (Hum. Mol. Genet., 3, 1117–1121 (1994)), and the like.

However, there have been no report relating to actions of the substance P analogs and the insulin-like growth factor on skin disorders.

From these facts, it is an interesting subject to combine the substance P analog with the insulin-like growth factor and to perform pharmacological tests on epidermis in order to study promotive effects on epidermal extension and promotive effects on skin wound healing.

DISCLOSURE OF THE INVENTION

The present inventors found by the above-mentioned tests that when a substance P analog, typically substance P or FGLM (SEQ ID NO: 2), coexists with an insulin-like growth factor, typically IGF-I, potentiation of these drugs promotes epidermal extension and skin wound healing remarkably and further exhibits an excellent effect of healing intractable diabetic skin ulcer. Namely, the skin wound healing promoters of the present invention comprising at least one of the substance P analogs and pharmaceutically acceptable salts thereof and the insulin-like growth factor as active ingredients have promotive effects on healing skin wounds such as rupture, abrasion, surgical incision, skin ulcer (including diabetic skin ulcer) and burn, and diseases such as gangrene originating from these skin wounds. To the skin wound healing promoters can be added ascorbic acid, ascorbate, a salt of ascorbic acid, pantothenic acid, a salt of pantothenic acid or the like, whose wound healing effects has been already recognized.

Examples of the substance P analogs are Tyr-Arg-Pro-Lys-Pro-Gln-Gln-Phe-Phe-Gly-Leu-Met-NH$_2$ (SEQ ID NO: 3), Arg-Pro-Lys-Pro-Gln-Gln-Phe-Phe-Gly-Leu-Met-NH$_2$ (substance P) (SEQ ID NO: 1), Arg-Pro-Lys-Pro-Gln-Gln-Phe-Tyr-Gly-Leu-Met-NH$_2$ (SEQ ID NO: 4), Tyr-Pro-Gln-Gln-Phe-Phe-Gly-Gln-Met-NH$_2$ (SEQ ID NO: 5), Pro-Gln-Gln-Phe-Phe-Gly-Leu-Met-NH$_2$ (SEQ ID NO: 6), Pro-Gln-Gln-Phe-Tyr-Gly-Leu-Met-NH$_2$ (SEQ ID NO: 7), Gln-Gln-Phe-Phe-Gly-Leu-Met-NH$_2$ (SEQ ID NO: 8), Asp-Ala-Phe-Tyr-Gly-Leu-Met-NH$_2$ (SEQ ID NO: 9), Gln-Phe-Phe-Gly-Leu-Met-NH$_2$ (SEQ ID NO: 10), Ala-Phe-Tyr-Gly-Leu-Met-NH$_2$ (SEQ ID NO: 11), Phe-Phe-Gly-Leu-Met-NH$_2$ (SEQ ID NO: 12), Tyr-Phe-Gly-Leu-Met-NH$_2$ (SEQ ID NO: 13), Gly-Phe-Gly-Leu-Met-NH$_2$ (SEQ ID NO: 14), Phe-Gly-Leu-Met-NH$_2$ (FGLM)(SEQ ID NO: 2) and Tyr-Gly-Leu-Met-NH$_2$ (SEQ ID NO: 16). Preferred examples of the substance P analogs are substance P and FGLM (SEQ ID NO: 2).

There are L-forms, D-forms and DL-forms as amino acid structures of the substance P analogs, and they are all included in the present invention. Preferred forms in the present invention are polypeptides wherein all steric structures are L-forms.

Examples of the pharmaceutically acceptable salts of the substance P analogs, substance P and FGLM (SEQ ID NO: 2) are hydrochlorides, sulfates, phosphates, lactates, maleates, fumarates, oxalates, methanesulfonates and p-toluenesulfonates.

The skin wound healing promoters of the present invention can be prepared by widely-used techniques. Examples of preparation forms thereof are ointments, jellies, calaplasms, applications, lotions, creams, sprays, aerosols, plasters, suspensions, emulsions, tablets and pills, and the promoters can also be used as liquid preparations by selecting a suitable solvent. In order to prepare the skin wound healing promoters, a filler, an excipient, a base, a disintegrator, a bulk filler, a binder, a film forming agent, a lubricant, a colorant, a pH adjustor, a solubilizer, a suspending agent, a buffer, a stabilizer, a preservative, an antiseptic, a surfactant, an antioxidant, a dispersant, an emulsifier, a dissolving agent, a solubilizing agent or the like can be added depending on their dosage forms.

Examples of vehicles or bases of the above-mentioned preparations are white soft paraffin, liquid paraffin, set hydrocarbons, cetyl alcohol, polyethylene glycol, gelatin, cornstarch, sodium alginate, methyl cellulose, hydroxyethyl cellulose, carboxymethyl cellulose, plastibase hydrophilic, gelatin, dextrin, cetyl alcohol, stearyl alcohol, polyethylene glycol, polyvinyl alcohol, methoxyethylene-maleic anhydride copolymers, polyvinyl ether, polymers and copolymers comprising vinylpyrrolidone as a polymer component, sodium stearate, magnesium stearate, benzalkonium chloride, fats and oils such as olive oil, camellia oil and soybean oil, lactose and water.

Each amount of the substance P analog and the pharmaceutically acceptable salt thereof contained in the skin wound healing promoter is 0.001 to 10% by weight, preferably 0.005 to 5% by weight. An amount of the insulin-like growth factor contained in the skin wound healing promoter is 0.0001 to 5% by weight, preferably 0.001 to 1% by weight.

The present invention provides a method of treating skin wounds comprising administering to a patient in need thereof a composition comprising effective amounts for treatment of the substance P analog or the pharmaceutically acceptable salt thereof and the insulin-like growth factor with a pharmaceutically acceptable additive.

The present invention also provides use of the substance P analogs or the pharmaceutically acceptable salts thereof and the insulin-like growth factors in the manufacture of therapeutic agents for skin wounds.

The skin wound healing promoters of the present invention can be administered in various forms depending on wound sites and degrees of wounds. For example, when the promoter is used as an external preparation, it is desirable to directly paint, spray or apply the promoter on required sites (affected parts) of skin.

The dosage of the skin wound healing promoters of the present invention can appropriately be selected in view of symptoms, age, dosage form and the like. Each usual daily dosage of the substance P analog and the pharmaceutically acceptable salt thereof is 0.01 to 5,000 mg, preferably 0.1 to 1,000 mg, which is given in a single dose or several divided doses, combined (mixed) with the insulin-like growth factor. Usual daily dosage of the insulin-like growth factor is 0.001 to 1,000 mg, preferably 0.01 to 500 mg, which is given in a single dose or several divided doses, combined (mixed) with at least one of the substance P analogs and the pharmaceutically acceptable salts thereof. The skin wound healing promoters of the present invention can be administered in a single dose to five doses per day.

Examples of preparations and results of pharmacological tests of the present invention are shown below. These examples do not limit the scope of the present invention, but are intended to make the present invention more clearly understandable.

BEST MODE FOR CARRYING OUT THE INVENTION

Formulation

Typical formulation examples of the present invention are shown below.

EXAMPLE 1

Ointment A-1

| In 100 g | |
| --- | --- |
| Substance P | 100 mg |
| IGF-I | 10 mg |
| Liquid paraffin | 10 g |
| White soft paraffin | q.s. |

Varying the amount of substance P, ointments having concentrations of 0.2% (w/w) (ointment A-2), 0.5% (w/w) (ointment A-3) and 1.0% (w/w) (ointment A-4) can be prepared.

EXAMPLE 2

Ointment B-1

| In 100 g | |
| --- | --- |
| FGLM | 100 mg |
| IGF-I | 5 mg |
| Liquid paraffin | 10 g |
| White soft paraffin | q.s. |

Varying the amount of FGLM (SEQ ID NO: 2), ointments having concentrations of 0.3% (w/w) (ointment B-2), 1% (w/w) (ointment B-3) and 2% (w/w) (ointment B-4) can be prepared.

EXAMPLE 3

Ointment C-1

| In 100 g | |
| --- | --- |
| FGLM | 50 mg |
| IGF-I | 10 mg |
| Ascorbic acid | 3 mg |
| Liquid paraffin | 10 g |
| Plastibase hydrophilic | qs. |

Varying the amount of FGLM (SEQ ID NO: 2), ointments having concentrations of 0.3% (w/w) (ointment C-2), 1% (w/w) (ointment C-3) and 3% (w/w) (ointment C-4) can be prepared.

Pharmacological Tests

(1) Action on Epidermal Extension

Excessive pentobarbital was administered to rats (Spraque-Dawley), and then ear tissue pieces of about 2×4 mm were prepared. Into a 60 mm Petri dish was put 18 ml of each TCM 199 culture medium containing each of test drugs in Table 1 [substance P, FGLM (SEQ ID NO: 2), IGF-I, substance P+IGF-I and FGLM (SEQ ID NO: 2)+IGF-I], and three tissue pieces were added to each Petri dish (12 samples: three sections per group). The tissue pieces were cultured in a $CO_2$ incubator (37° C.·5% $CO_2$) for 24 hours, the tissue pieces were fixed with ethanol-acetic acid (volume ratio 95:5) to prepare three tissue sections per tissue piece according to the conventional method. The tissue sections were stained with hematoxylin-eosin, and then length of a epidermal cell layer having extended cut surfaces was measured. The tissue pieces were cultured under the same condition as mentioned above using a culture medium containing no test drug to prepare controls. These results are shown in Table 1. The values in the table are the average of 12 samples.

TABLE 1

| Test drugs | Extension length of epidermis (μm) |
| --- | --- |
| Control | 63.02 |
| Substance P (20 μM) | 72.57 |
| FGLM (20 μM) | 55.37 |
| IGF-I (10 ng/ml) | 50.68 |
| Substance P (20 μM) + IGF-I (10 ng/ml) | 156.04 |
| FGLM (20 μM) + IGF-I (10 ng/ml) | 138.24 |

(2) Action on Skin Wound Healing

Streptozotocin (70 mg/kg BW) dissolved in a citric acid buffer was injected intravenously into tails of rats (Wistar) under diethyl ether inhalation anesthesia to prepare diabetes rats (DM Rat) (five rats per group). An equal amount of the citric acid buffer alone was injected intravenously into rats (Wistar) to prepare non-diabetes rats (non DM Rat) (five rats per group). Four weeks after the intravenous injection, the back of all the rats was shaved with hair clippers under diethyl ether inhalation anesthesia, and hair was removed with cream for depilation. After 24 hours, five full-thickness (i.e. epidermis and dermis) wounds were made on back skin in equal intervals with a trepan for skin biopsy having a diameter of 5 mm. Confirming hemostasis, each ointment in Tables 2 and 3 was applied on the wound once a day. Just before applying the ointment once a day, the back wounds were photographed, and their areas were measured. Table 2 shows results of measurement of areas for the non-diabetes rats (non DM Rat), and Table 3 shows results of measurement of areas for the diabetes rats (DM Rat). The values in these tables are the average of five samples.

TABLE 2

| Ointment group | Skin wound area of non-diabetes rat (%) | | | |
| --- | --- | --- | --- | --- |
| | 1st day | After 2 days | After 4 days | After 6 days |
| Control (PBS) | 100 | 93 | 87 | 64 |
| Substance P (2.5 mg/ml) | 100 | 88 | 74 | 59 |
| IGF-I (1 μg/ml) | 100 | 81 | 66 | 43 |
| Substance P (2.5 mg/ml) + IGF-I (1 μg/ml) | 100 | 72 | 50 | 32 |

TABLE 3

| Ointment group | Skin wound area of diabetes rat (%) | | | | |
| --- | --- | --- | --- | --- | --- |
| | 1st day | After 1 day | After 4 days | After 7 days | After 10 days |
| Control (PBS) | 100 | 96 | 91 | 84 | 60 |
| Substance P (2.5 mg/ml) | 100 | 90 | 77 | 68 | 44 |
| IGF-I (1 μg/ml) | 100 | 89 | 64 | 52 | 27 |
| Substance P (2.5 mg/ml) + IGF-I (1 μg/ml) | 100 | 81 | 50 | 18 | 1 |

Table 1 explicitly shows that even if the tissue pieces are cultured by using each of substance P, FGLM (SEQ ID NO: 2) and IGF-I solely, epidermal extension is almost as long as that in the case where the control is used (without additive), whereas when the tissue pieces are cultured by coexistence of substance P or FGLM (SEQ ID NO: 2) with IGF-I, extension is 2 to 2.5 times longer than that in the case where these drugs are used solely (synergistic effect). Table 2 shows that the ointment containing substance P and IGF-I promotes skin wound healing more remarkably than the case where substance P or IGF-I is used solely. Table 3 shows that the ointment containing substance P and IGF-I exhibits an excellent effect on intractable diabetes rats (DM Rat), too. Accordingly, administration of at least one of the substance P analogs, typically substance P and FGLM (SEQ ID NO: 2), and pharmaceutically acceptable salts combined (mixed) with the insulin-like growth factor, typically IGF-I, can promote effectively healing of skin wounds such as rupture, abrasion, surgical incision, skin ulcer, particularly intractable skin ulcer of diabetes patients and burn by potentiation of these drugs.

INDUSTRIAL APPLICABILITY

The present invention provides skin wound healing promoters comprising at least one of substance P analogs and pharmaceutically acceptable salts thereof and an insulin-like growth factor as active ingredients.

What is claimed is:

1. A method of treating a wound to a surface tissue, wherein the surface tissue consists of skin, comprising administering to a patient in need thereof a composition comprising effective amounts for treatment of a substance P analog which is Phe-Gly-Leu-Met-$NH_2$ (SEQ ID NO: 2) as a unit or a pharmaceutically acceptable salt thereof, and insulin-like growth factor-I, as active ingredients.

2. The method of treating a skin wound as claimed in claim 1, wherein the skin wound is a rupture, an abrasion, a surgical incision, a skin ulcer or a burn.

3. The method of treating a skin wound as claimed in claim 1, wherein said skin wound is a diabetic skin ulcer.

4. A method of treating a wound to a surface tissue, wherein the surface tissue consists of skin, comprising administering to a patient in need thereof a composition comprising 0.001 to 10% by weight of a substance P analog which is Phe-Gly-Leu-Met-$NH_2$ (SEQ ID NO: 2) as a unit or a pharmaceutically acceptable salt thereof and 0.0001 to 5% by weight of insulin-like growth factor-I, as active ingredients.

5. The method of treating a skin wound as claimed in claim 4, wherein the substance P analog is in an amount of 0.005 to 5% by weight.

6. The method of treating a skin wound as claimed in claim 4, wherein the insulin-like growth factor-I is in an amount of 0.001 to 1% by weight.

7. The method of treating a skin wound as claimed in claim 5, wherein the insulin-like growth factor-I is in an amount of 0.001 to 1% by weight.

8. The method of treating a skin wound as claimed in claim 4, wherein the skin wound is a rupture.

9. The method of treating a skin wound as claimed in claim 4, wherein the skin wound is an abrasion.

10. The method of treating a skin wound as claimed in claim 4, wherein the skin wound is a skin ulcer.

11. The method of treating a skin wound as claimed in claim 4, wherein the skin wound is a burn.

12. The method of treating a skin wound as claimed in claim 4, wherein the skin wound is a diabetic skin wound.

* * * * *